(12) United States Patent
Foran et al.

(10) Patent No.: US 6,581,598 B1
(45) Date of Patent: Jun. 24, 2003

(54) POSITIVE EXPIRATORY PRESSURE DEVICE

(75) Inventors: Jennifer M. Foran, Bridgeport, NY (US); Lawrence A. Weinstein, Oneida, NY (US); Fredrick M. Richards, Clinton, NY (US); Christopher T. Zirps, Milton, MA (US); Robert H. Elden, Cambridge, MA (US)

(73) Assignee: DHD Healthcare Corporation, Wampsville, NY (US)

( * ) Notice: Subject to any disclaimer, the term of this patent is extended or adjusted under 35 U.S.C. 154(b) by 0 days.

(21) Appl. No.: 09/449,208

(22) Filed: Nov. 24, 1999

(51) Int. Cl.[7] ............................................. A61M 16/00
(52) U.S. Cl. ............................. 128/204.23; 128/204.19; 128/205.24
(58) Field of Search ........................... 482/13; 600/540, 600/538; 128/202.22, 205.23, 205.24, 204.19, 204.23

(56) References Cited

U.S. PATENT DOCUMENTS

| | | | | |
|---|---|---|---|---|
| 2,918,917 A | * | 12/1959 | Emerson | 128/204.21 |
| 3,710,780 A | * | 1/1973 | Milch | 128/25 R |
| 4,221,381 A | * | 9/1980 | Ericson | 272/99 |
| 4,327,740 A | * | 5/1982 | Shuman | 128/728 |
| 4,601,465 A | * | 7/1986 | Roy | 272/99 |
| 4,611,591 A | * | 9/1986 | Inui et al. | 128/204.21 |
| 4,651,731 A | * | 3/1987 | Vicenzi et al. | 128/204.25 |
| 4,739,987 A | * | 4/1988 | Nicholson | 272/99 |
| 4,973,047 A | * | 11/1990 | Norell | 272/99 |
| 5,027,809 A | * | 7/1991 | Robinson | 128/203.24 |
| 5,065,746 A | * | 11/1991 | Steen | 128/204.18 |
| 5,067,707 A | * | 11/1991 | Kohnke | 272/99 |
| 5,193,529 A | * | 3/1993 | Labaere | 128/200.24 |
| 5,439,430 A | * | 8/1995 | Rubens et al. | 482/13 |
| 5,451,190 A | * | 9/1995 | Liardet | 482/13 |
| 5,540,220 A | * | 7/1996 | Gropper et al. | 128/204.21 |
| 5,547,440 A | * | 8/1996 | Rubens et al. | 482/13 |
| 5,632,298 A | * | 5/1997 | Artinian | 137/102 |
| 5,658,221 A | * | 8/1997 | Hougen | 482/13 |
| 5,791,339 A | * | 8/1998 | Winter | 128/202.22 |
| 5,890,998 A | * | 4/1999 | Hougen | 482/13 |
| 5,899,832 A | * | 5/1999 | Hougen | 482/13 |
| 5,910,071 A | * | 6/1999 | Hougen | 482/13 |
| 6,058,932 A | * | 5/2000 | Hughes | 128/200.24 |
| 6,083,141 A | * | 7/2000 | Hougen | 482/13 |
| 6,102,038 A | * | 8/2000 | DeVries | 128/204.23 |

* cited by examiner

*Primary Examiner*—Weilun Lo
*Assistant Examiner*—Mital Patel
(74) *Attorney, Agent, or Firm*—August E. Roehrig, Jr.; Hancock & Estabrook, LLP

(57) ABSTRACT

An enhanced PEP therapy device which provides a variable frequency and variable magnitude positive expiratory pressure by utilizing a nonlinear orifice for adjusting and maintaining a desired positive expiratory pressure oscillation in accordance with a predetermined pressure range of a patient's expiratory air.

9 Claims, 8 Drawing Sheets

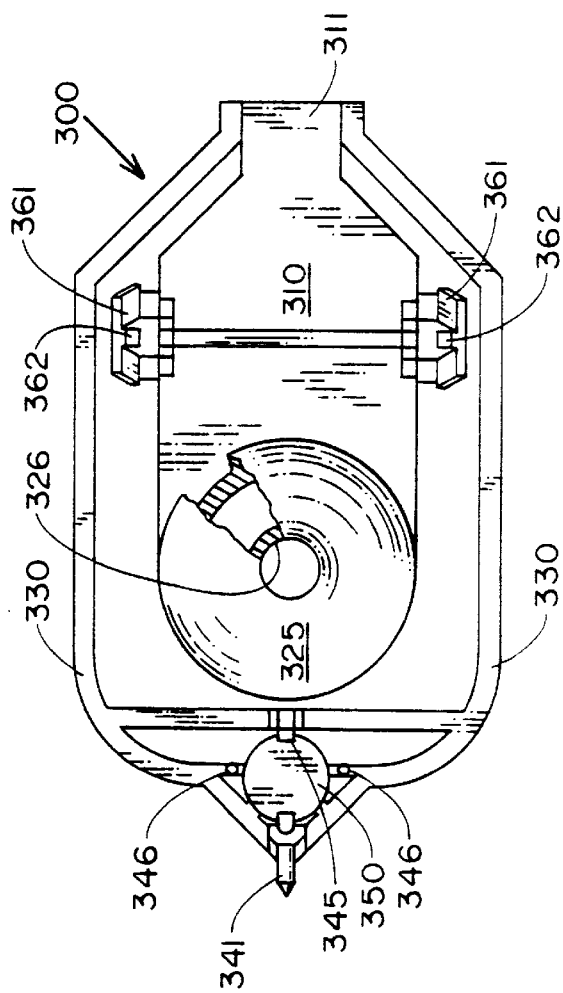
FIG. 5
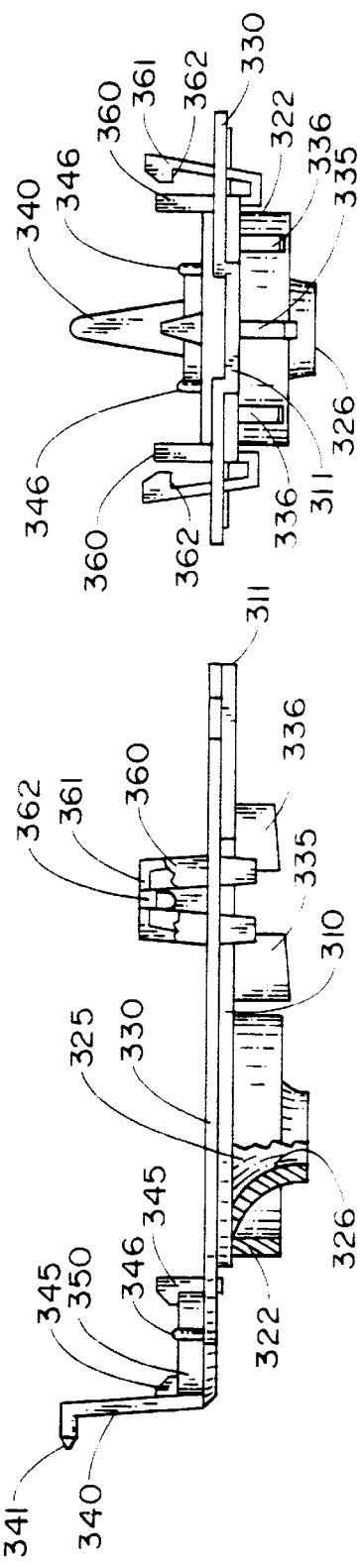
FIG. 6
FIG. 4

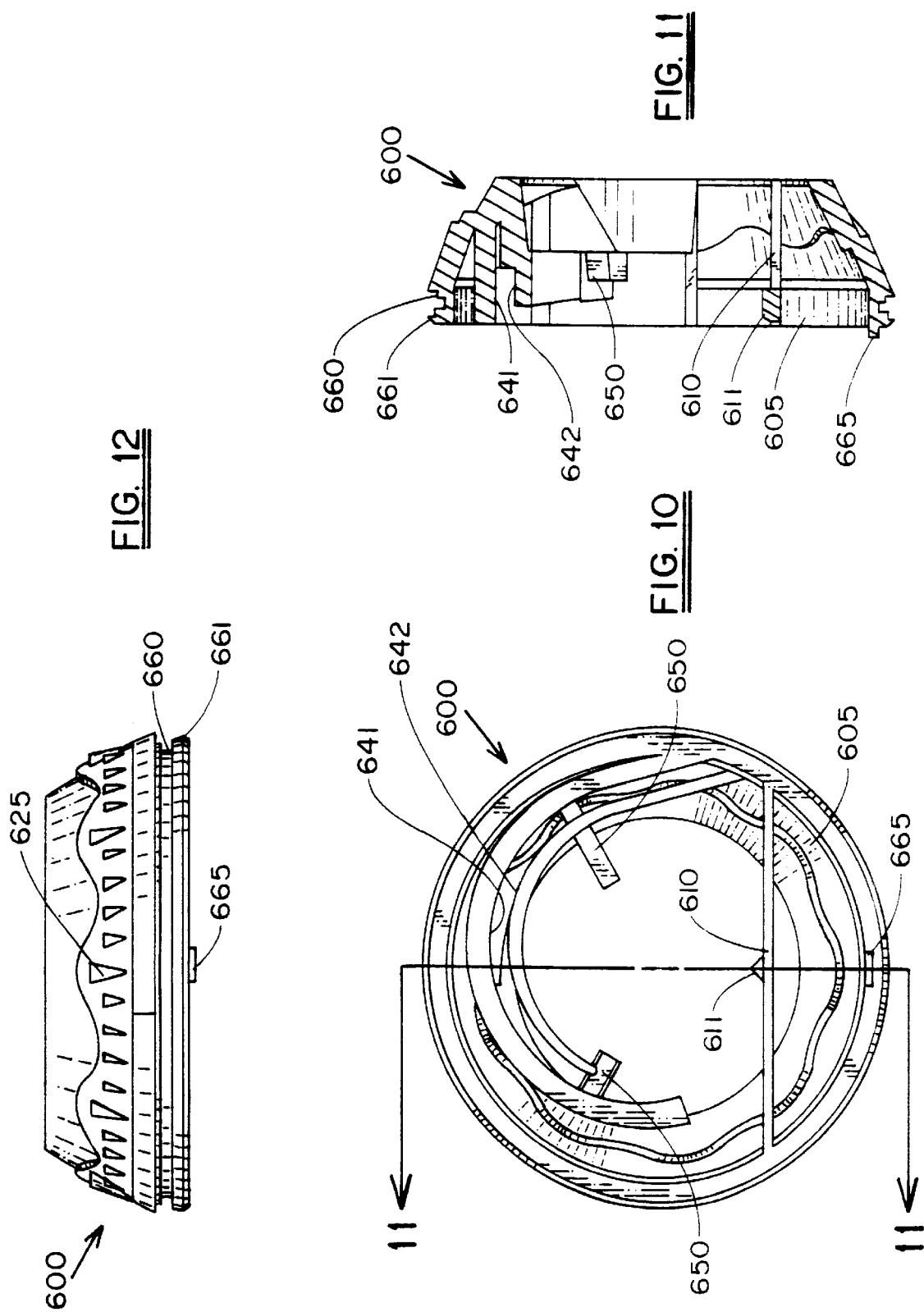

POSITIVE EXPIRATORY PRESSURE DEVICE

TECHNICAL FIELD

This invention relates in general to a hand-held, single patient use, positive expiratory pressure respiratory therapy device and, in particular, to a positive expiratory pressure respiratory therapy device utilizing a nonlinear orifice for adjusting and maintaining a desired pressure oscillation frequency in accordance with a predetermined pressure range of a patient's expiratory air.

BACKGROUND ART

Persons who suffer from pulmonary problems that result in large amounts of mucus being produced in the lungs often require assistance in the removal of these secretions. If these secretions are allowed to remain in the lungs, airway obstruction occurs resulting in poor oxygenation and possible pneumonia and/or death. One of the clinically recognized treatments for this condition is a technique known as positive expiratory pressure therapy or PEP. With PEP therapy, a patient exhales against a resistance to generate expiratory pressure at a substantially constant rate of flow. Prescribed expiratory pressures are generally in the range of 10–20 cm H2O, although other pressure ranges and pressures can be used.

PEP therapy has been documented by clinical research as equal to or superior to standard chest physiotherapy techniques which, while effective, are time consuming and not well tolerated by many patients who have difficulty breathing for extended periods of time in certain positions required for administration of standard chest physiotherapy. Accordingly, PEP therapy is believed to provide significant advantages to patients suffering from cystic fibrosis, and is felt to be an eventual replacement for chest physiotherapy for many patients.

In the use of PEP therapy, a patient breathes through an orifice restricter to generate a positive pressure in the lungs during exhalation, with the pressure falling to zero at the end of exhalation. By selection of a proper-sized orifice, a given pressure is determined for the exhalation flow rate generated by an individual patient. This extended, substantially constant flow, elevated-pressure exhalation has been shown to be effective for moving secretions trapped in the lungs to the larger airways where the secretions can then be removed through coughing.

The PEP therapy devices presently in use are very effective in the administration of the aforementioned type of PEP therapy. While an expensive pressure gauge can be connected to such a device to display the expiratory pressure being exerted by the patient, proper administration of the PEP therapy does not require the determination by the patient of an exact gauge pressure. Accordingly, PEP therapy can be properly administered as long as the patient can be made aware that the expiratory pressure is being maintained within a proper predetermined pressure range. Such a satisfactory PEP therapy device is disclosed in R. A. Niles et al U.S. Pat. No. 5,598,839, POSITIVE EXPIRATORY PRESSURE DEVICE, wherein a single user respiratory therapy device includes a pressure range monitoring unit which provides a patient with a visual feed-back to monitor the correct use of a PEP device for enhancing the benefits of positive expiratory pressure therapy.

It has also been found that in the treatment of patients having chronic obstructive pulmonary disease (COPD), chronic bronchitis, cystic fibrosis, atelectasis, or other conditions producing retained secretions, treatment with PEP therapy is improved by combining positive expiratory pressure therapy with airway oscillation and intermittent airflow acceleration. Some studies of chronic bronchitis patients have shown that 86% were able to expectorate mucus easier and more efficiently compared to 48% in a control group, and in another study, mucus clearance increased from 2.8 ml to 10.1 ml through the use of such enhanced PEP therapy.

The present invention comprises an enhanced PEP therapy device which provides a variable frequency positive expiratory pressure by utilizing a nonlinear orifice for adjusting and maintaining a desired pressure oscillation frequency in accordance with a predetermined pressure range of a patient's expiratory air.

SUMMARY OF THE INVENTION

It is, therefore, an object of this invention to improve positive expiratory pressure devices.

Another object of this invention is to utilize a variable frequency expiratory pressure in a positive expiratory pressure therapy device.

A further object of this invention is obtain a variable frequency positive pressure in a positive expiratory pressure device by utilizing a nonlinear orifice to adjust and maintain a predetermined pressure oscillation frequency.

These and other objects are attained in accordance with the present invention wherein there is provided a hand-held, single patient use, positive expiratory pressure respiratory therapy device utilizing a nonlinear orifice for adjusting and maintaining a desired pressure oscillation frequency in accordance with a predetermined pressure range of a patient's expiratory air.

BRIEF DESCRIPTION OF THE DRAWINGS

Further objects of the invention together with additional features contributing thereto and advantages accruing therefrom will be apparent from the following description of a preferred embodiment of the invention which is shown in the accompanying drawings with like reference numerals indicating corresponding parts throughout, wherein:

FIGS. 4, 5 and 6 are, respectively, a front profile, top elevation and right side profile view of an adjustable orifice platform portion of the invention to illustrate the nonlinear orifice and a portion of the structure by which the magnitude and the frequency of the oscillatory positive expiration pressure can be adjusted;

FIGS. 10, 11 and 12 are, respectively, a front profile, section and top elevation of an adjustment dial portion of the invention to illustrate the manner in which the adjustable platform portion of the invention is moveable relative to the rocker portion to determine the oscillatory movement of the rocker portion;

BEST MODE FOR CARRYING OUT THE INVENTION

Figure 1:
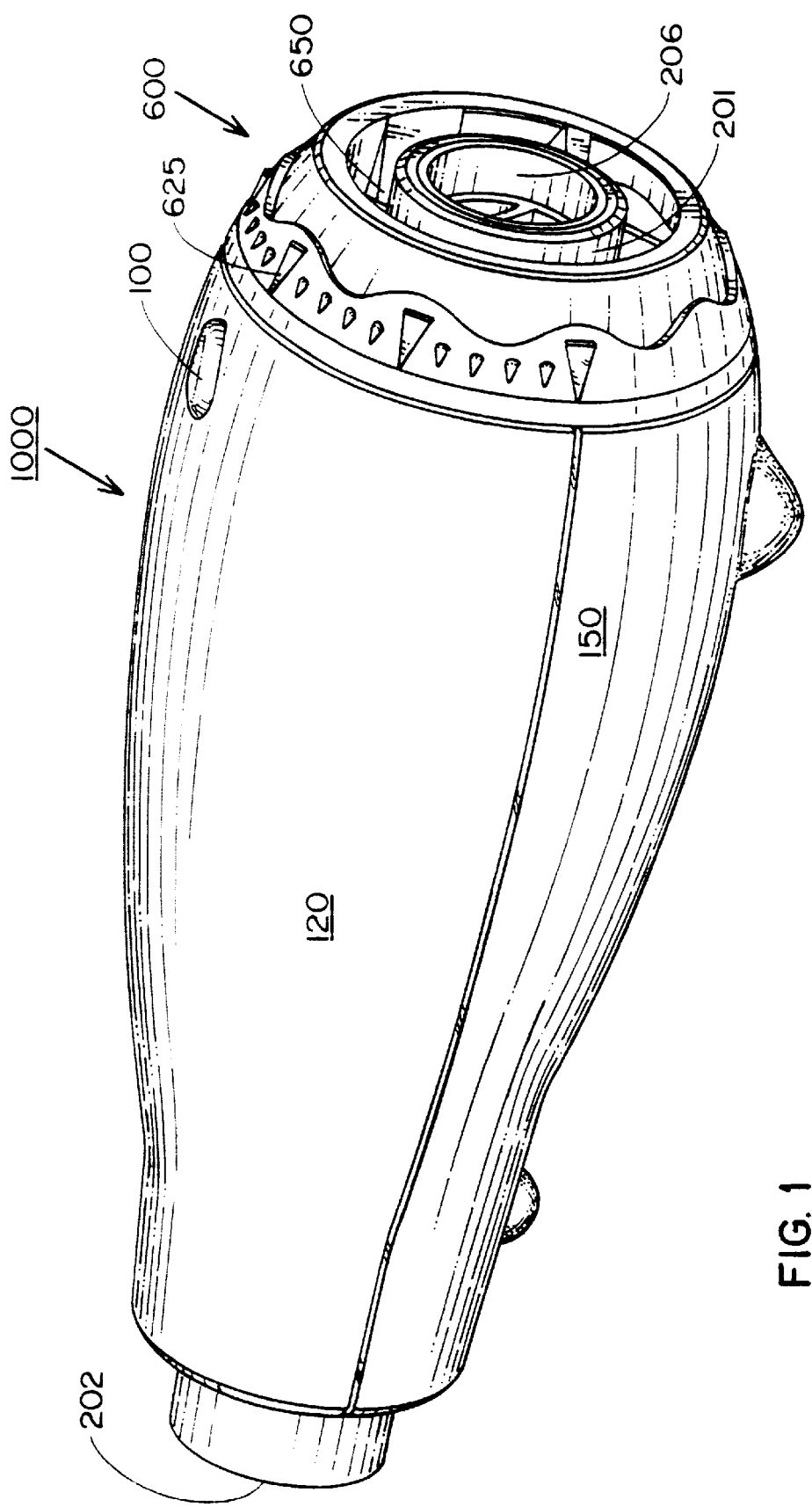
FIG. 1 is a perspective view of the assembled invention.
Figure 2:
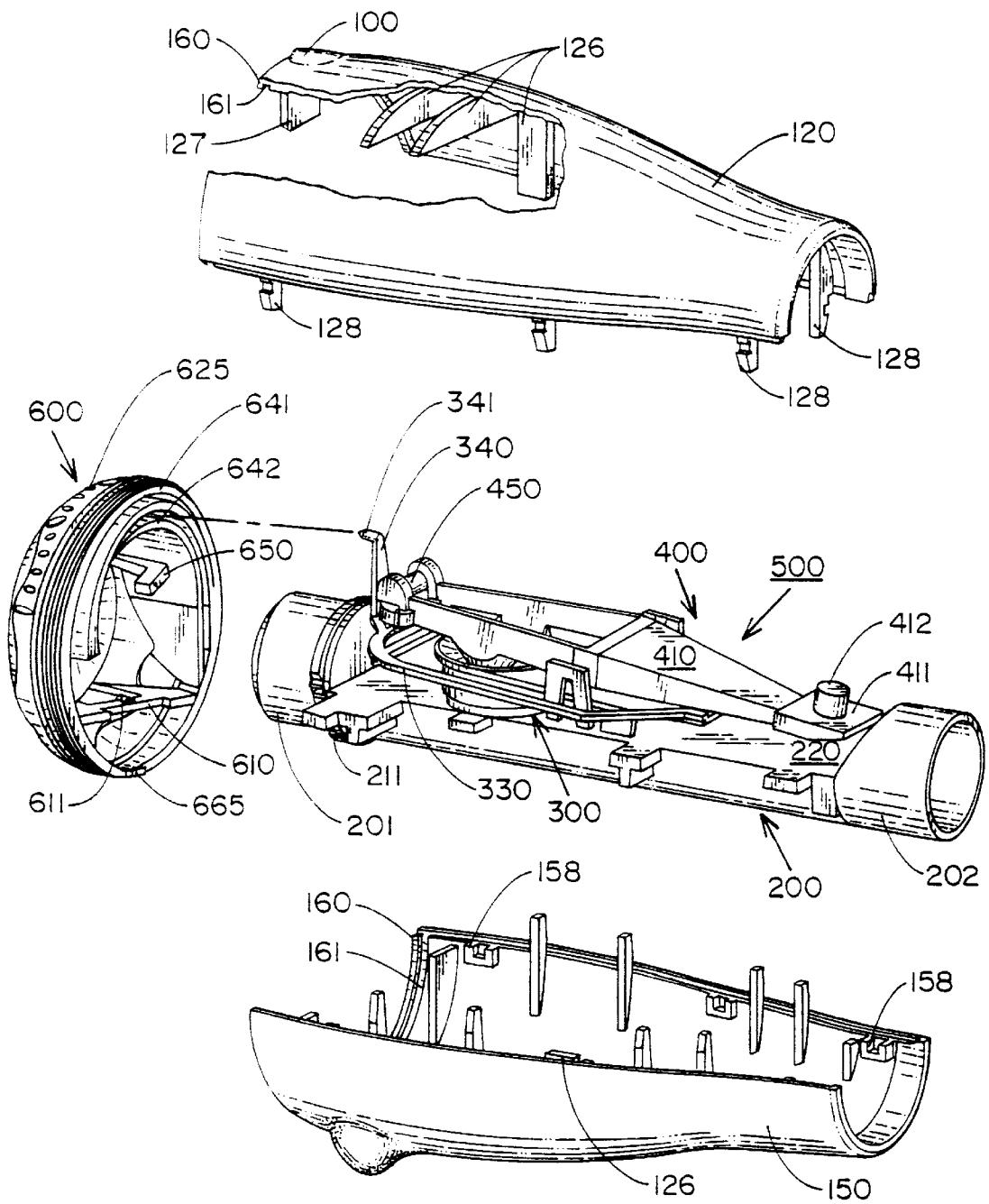
FIG. 2 is an exploded perspective view of the invention with portions removed to better illustrate the internal structure thereof.

Referring now to the drawings, there is illustrated in FIGS. 1 and 2 a hand-held, single patient user, positive expiratory pressure respiratory therapy device 1000 having a nonlinear orifice to provide a desired pressure oscillation frequency of the user's expiratory air. The device 1000 includes an expiratory air driven oscillatory rocker assembly 560 carried within a housing formed in two portions, an upper housing portion 120 and a lower housing portion 150. A rotatable adjusting dial 600 is carried at an inspiratory air inlet end 201 of an air flow tube 200, and functions in a manner to be described hereinafter in detail to adjust the magnitude and the frequency of the user's exhalation pressure.

Figure 3:
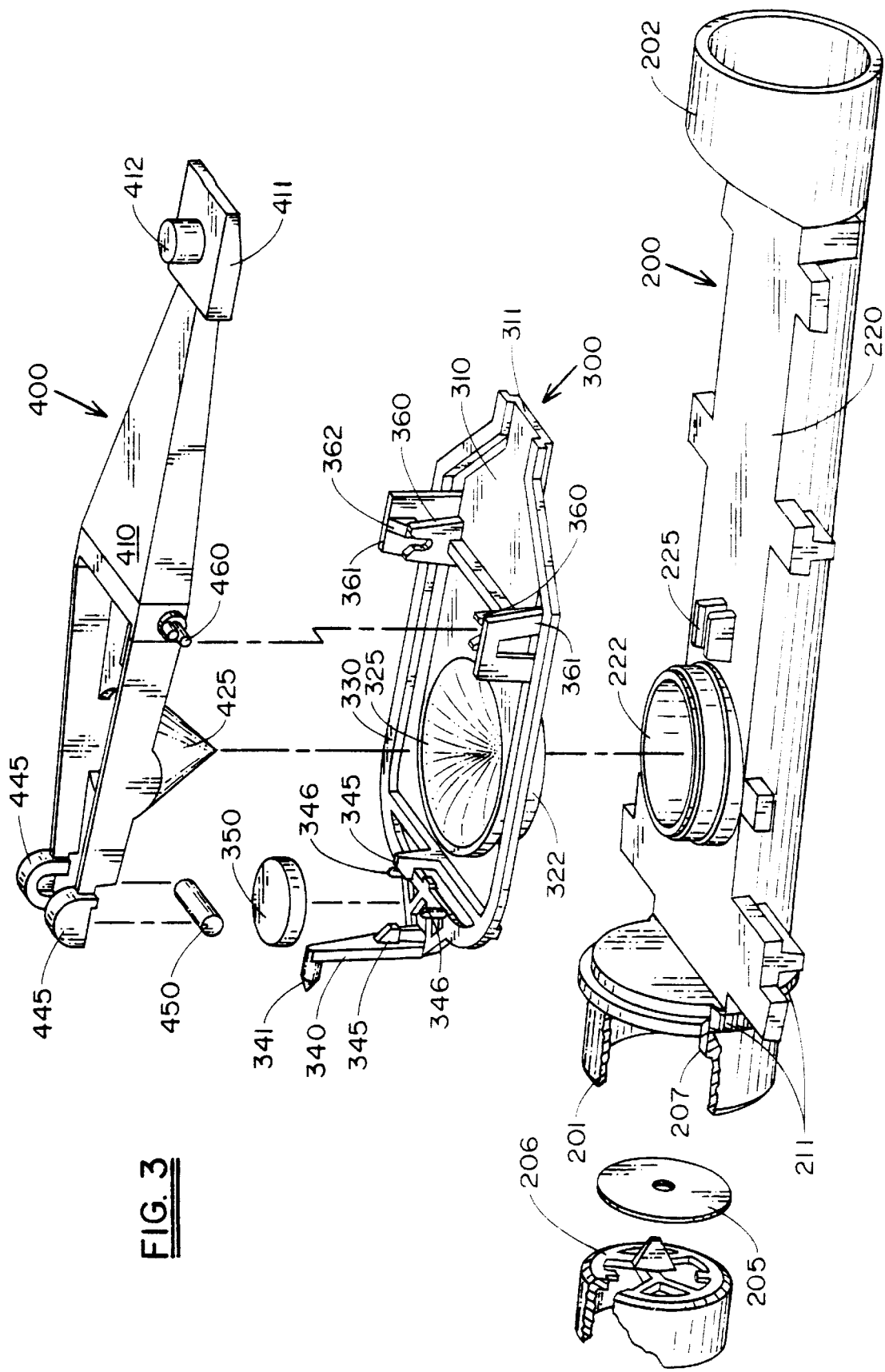
FIG. 3 is an exploded perspective view of a portion of the invention to better illustrate the manner in which a user produces an oscillatory positive expiratory pressure, and a portion of invention through which the magnitude and the frequency of the positive expiratory pressure can be adjusted.
Figure 9:
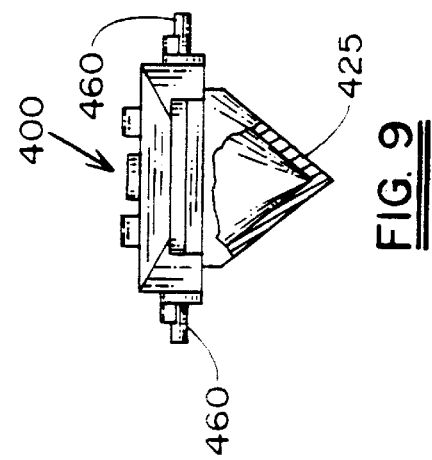
FIGS. 7, 8 and 9 are, respectively, a front profile, top elevation and right side profile view of a rocker portion of the invention with portions broken away to show the internal structure which forms a portion of the device by which the user produces an oscillatory positive expiration pressure.
Figure 8:
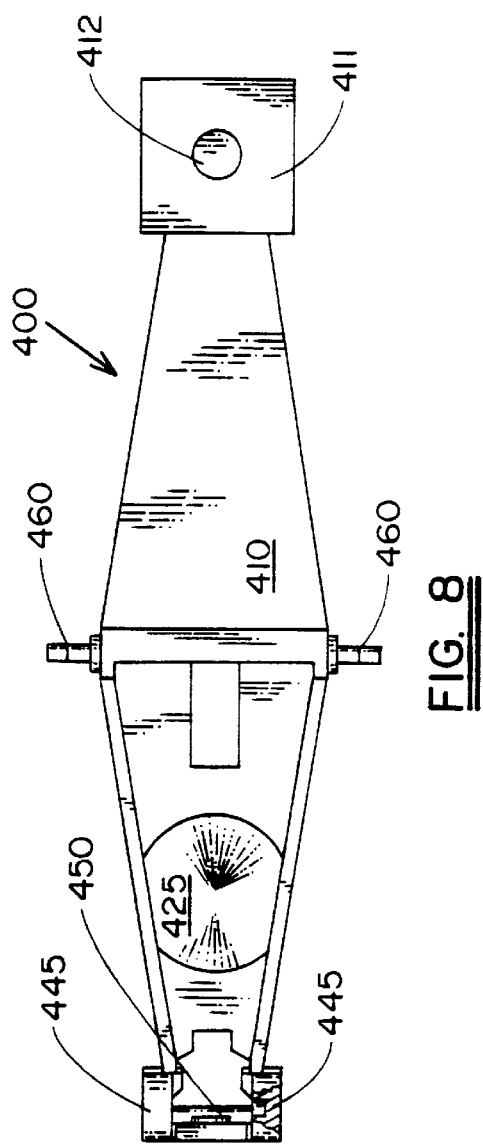
Figure 7:
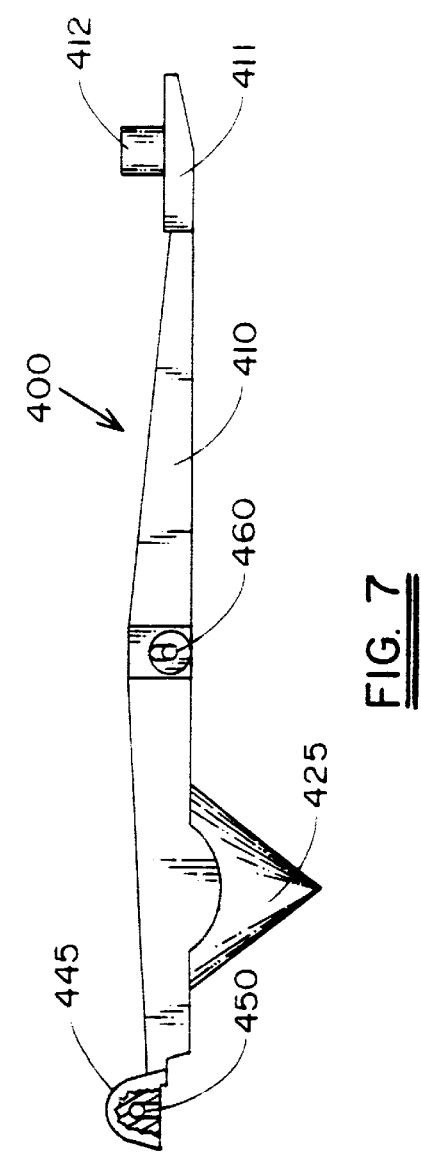

The expiratory air driven oscillatory rocker assembly 500 is illustrated in the exploded view of FIG. 3, and the components thereof are illustrated in more detail in FIGS. 4–9. Referring in particular to FIG. 3, there is illustrated an air flow tube 200 having the inspiratory air inlet end 201 at one end and a patient input end 202 through which a patient inhales inspiratory air and discharges expiratory air. The inspiratory air inlet 201 and the patient input end 202 of the air flow tube 200 are sized as a 22 mm male fitting. In this manner the air flow tube 200 can be used with a standard detachable mouthpiece or a mask of the type used with positive expiratory pressure respiratory therapy, or additional respiratory therapy equipment, such as a nebulizer or MDI spacer, having a standard female fitting to be received on such a fitting, also may be used with the invention.

The air flow tube 200 is open throughout its length, and includes at the inspiratory air inlet end 201 a one-way flapper valve 205. The flapper valve 205 allows a patient to draw inspiratory air into the air flow tube 200 through the air inlet end 201, but prevents expiratory air from being passed out of the air flow tube 200 through the air inlet end. To this end the one way flapper valve 205 is positioned on a spider 206 which is inserted into the open air inlet end 201 against a shoulder 207 forming a space sufficient for the one way operation of the valve 205. Upon inhalation by a user, the valve 205 opens and allows air to pass into the air flow tube 200. Upon exhalation, the valve 205 is held closed against the spider 206 thereby preventing expiratory air from passing out through the inlet end 201.

The portion of the hollow air flow tube 200 between the inlet end 201 and the patient input end 202 includes a flat support platform 220 upon which the structures which create the patient induced oscillatory positive expiratory air pressure are carried. To this end the support platform 220 includes a cylindrical collar or cowling 222 defining an air passage into the interior of the hollow air flow tube 200, and a pair of spaced abutments 225 into which portions of an adjustable orifice platform 310 of a magnet carriage 300 are secured.

As best seen in FIG. 3, the collar 222 is downwardly tapered from a forward portion positioned toward the air inlet end 201 to a rear portion positioned toward the patient input end 202 to better accommodate the positioning of a complementary circular coupling portion 322 over the collar 222 to secure the adjustable orifice platform 310 to the air flow tube 200, and position the tapered conical interior surface 325 of the coupling 322 within the cowling 222. In this manner the tapered conical interior surface 325 closes the air passage into the air flow tube 200 except for a circular opening 326 which extends downwardly, as best illustrated in FIGS. 4 and 6, through the collar 222 into the hollow interior of the air flow tube 200.

A pivotal magnet support 330, which depends from the adjustable orifice platform 310, in combination with a rocker assembly 400, forms a mechanism by which the discharge of a patient or user's expiratory air can be periodically interrupted to create a pulsating wave form, the frequency and magnitude of which can be adjusted between defined limits in accordance with the positive expiratory pressure treatment or therapy desired by a physician or clinician. To this end the adjustable orifice platform 310 is positioned on the cowling 222 of the air flow tube 200 at a slight incline in the direction from the patient input end 202 towards the air inlet end 201 at a slope equal to the slope of the cowling 222 to which the circular coupling portion 322 is attached. A tang 335 carried on the longitudinal centerline of the platform 310 is positioned to engage the spaced abutments 225 formed on the support platform 220 to help secure and position the adjustable orifice platform 310 on the air flow tube 200. A pair of support bosses 336 extend downwardly from the platform 310 into contact with the support platform 220 of the air flow tube 200 to properly position the adjustable orifice platform 310 relative thereto. The contact surfaces where the tang 335 and each of the bosses 336 contact the support platform 220 are tapered to assist in this positioning.

The adjustable orifice platform 310 also includes the pivotal magnet support 330 which is connected to the orifice platform 310 at an end 311 of the platform. The pivotal magnet support extends out from the end 311 encircling, but spaced from, the remainder of the platform 310 for pivotal movement relative thereto. The free end of the pivotal magnet support 330 terminates in a cam follower 340, which extends upwardly from the remainder of the magnet support 330, and has a tip 341 on the terminal portion thereof which extends horizontally in a plane substantially parallel to that of the encircling portion of the pivotal magnet support 330 for engaging a cam surface formed in the interior of the rotatable adjusting dial 600, as illustrated in FIG. 2. In this manner, the relative position between the adjustable orifice platform 310 and the pivotal magnet support 330 can be set by rotating the rotatable adjusting dial 600.

As best shown in FIGS. 3–6, a magnet 350 is carried by the pivotal magnet support 330 at a position adjacent the base of the cam follower 340. The magnet 350 is held in position on the support 330 by a pair of engaging tabs 345 which are carried by the support and extend upwardly therefrom. Each of the engaging tabs 345 has a shoulder portion which engages a portion of the magnet 350 to secure the magnet 350 to the pivotal magnet support 330. A pair of guides 346 are also carried by the support 330 and assist in retaining the magnet 350 in a secured position on the support 330.

As previously disclosed, the pivotal magnet support 330, the adjustable orifice platform 310 and the rocker assembly 400 form an expiratory air driven oscillatory rocker assembly 500 by which the expiratory air discharge of a patient or user can be periodically interrupted to create a pulsating wave form, the frequency and magnitude of which can be adjusted between defined limits in accordance with the positive expiratory pressure treatment or therapy desired by a physician or clinician. To this end the adjustable orifice platform 310 includes a pair of spaced pivot supports 360 forming a pivot axis which lies in a plane above and extends transverse to the longitudinal axis of the pivotal magnet support 330 and the adjustable orifice platform 310, as best seen in FIGS. 4–6. These pivot supports 360 receive the pivot pins 460 of the rocker assembly 400 upon which the rocker assembly 400 is pivotally moveable. One of a pair of locking guides 361 is positioned adjacent each of the pivot supports 360 to limit the axial movement of the rocker assembly 400 relative to the magnet carriage 300, and an overhanging shoulder portion 362 on each of the guides 361 prevents vertical movement of the rocker assembly pivot pins 460. In this manner the rocker assembly 400 remains pivotable on the pivot pins 460 regardless of the orientation of the device 1000 allowing the patient to receive therapy and use the device in any position.

The rocker assembly 400, best illustrated in FIGS. 3 and 7–9, is balanced for pivotal movement about the pivot pins 460. To this end a balancing pad 411 and balancing cylinder 412 are formed at one end of the rocker platform 410, to balance the weight of a flow cone 425 and a steel rod 450 carried at the opposite end of the rocker platform. The flow cone 425 is sized and positioned to be inserted into the tapered conical interior 325 of the coupling 322 for closing the circular opening 326 into the air tube 200.

The steel rod 450 is carried at the end opposed to the balancing pad 411 and balancing cylinder 412, in a pair of bifurcated mounting pads 445 which retain the ends of the steel rod 450 while allowing the remaining portion of the rod to be exposed. In this manner, the steel rod is exposed to the magnetic field of the magnet 350, and will be drawn thereto in accordance with the strength of the magnetic field and any force being exerted on the rocker platform 410 in opposition to the magnetic field.

Figure 13:
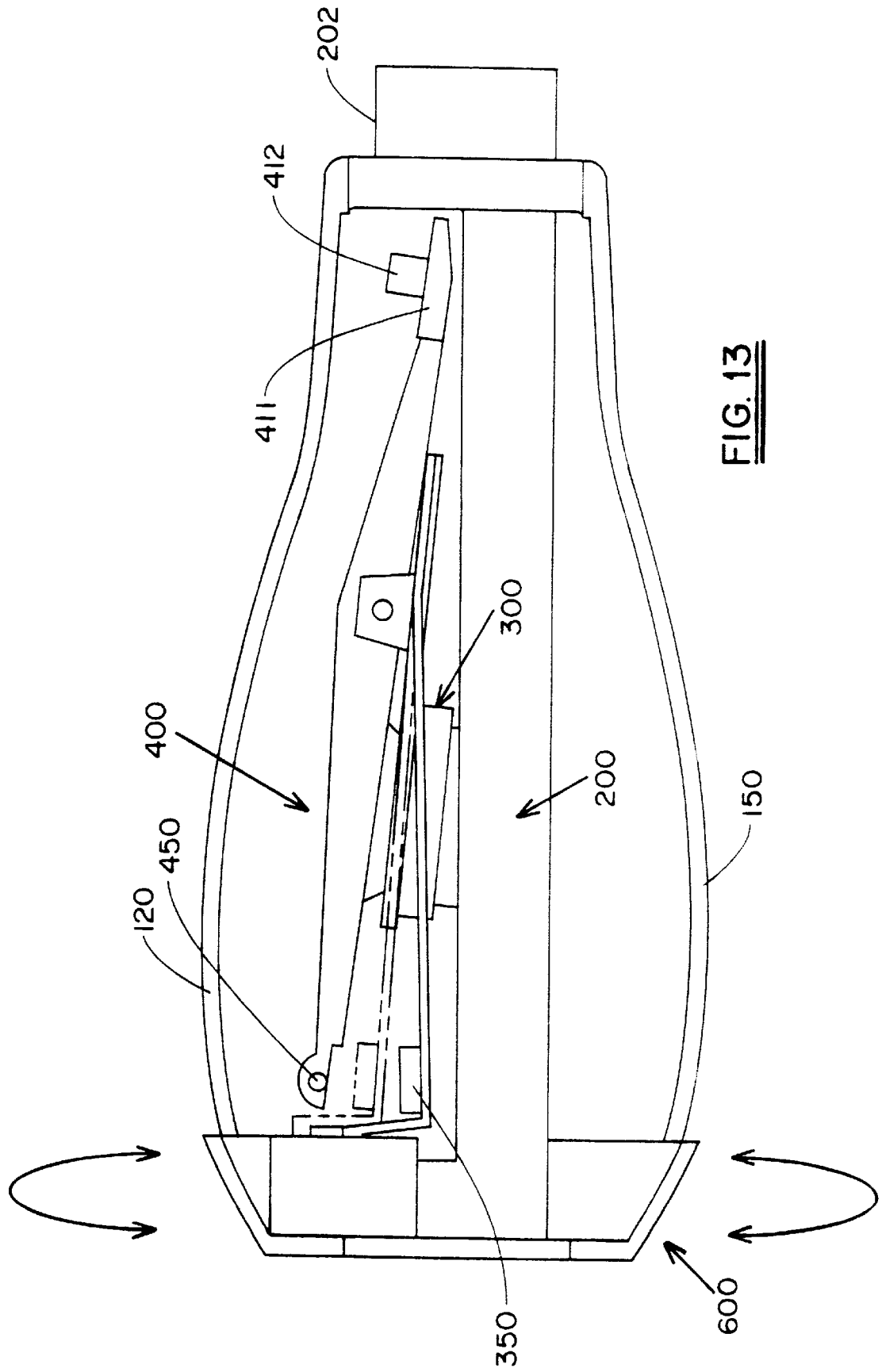
FIG. 13 is a mechanical schematic representation of the invention to better illustrate the operation thereof in response to changes in the magnetic field.

To control the strength of the magnetic field being applied to the steel rod 450 by the magnet 350, the spacing therebetween is set by the operation of the rotatable adjusting dial 600, best illustrated in FIGS. 2 and 10–12. Rotation of the adjusting dial 600 acts on the tip 341 of the cam follower 340 through a pair of upper and lower parallel cam surfaces 641 and 642, respectively, formed on the interior of the adjusting dial. The cam surfaces 641 and 642 are formed as upper and lower parallel spaced walls into which the tip 341 of the cam follower 340 is inserted so that the vertical movement of the tip 341 will be determined by its position between the upper and lower cam surfaces. As illustrated diagramatically in FIG. 13, rotation of the adjusting dial 600 will move the magnet 350 from a position shown in solid lines wherein the magnet is at a maximum spacing from the steel rod 450, and thereby exerts a decreased magnet attracting force, to a position illustrated in phantom wherein the magnet is illustrated at a minimum spacing to the steel rod 450 whereby a maximum magnetic field attracting force will be exerted. While the device 1000 will function to provide an oscillatory positive expiratory pressure pulse without the use of the magnetic field between the magnet 350 and steel rod 450 because of the opening and closing of the orifice 326 by the movement of the cone 425 in response to the patient or user's expiratory air pressure, the use of the magnetic field permits the device 1000 to provide an adjustable range in the pressure of the patient's expiratory air discharge required to create the oscillatory positive expiratory pressure pulses.

To assist a patient or user in using the device once the proper magnetic field has been set, a plurality of indicia 625 are spaced about the periphery of the adjusting dial 600. The indicia 625, in combination with a base reference point 100 on the upper housing 120, are used to ensure that the correct setting is being maintained after the physician or clinician has established the desired level for treatment. To minimize the occurrence of the rotatable adjusting dial 600 being unknowingly rotated, a sounding board 610 is formed, such as by a thin chord of plastic material from which the adjusting dial is constructed, which extends across the lower internal portion of the adjusting dial 600 forming a chord portion joined to an inner wall 605 of the dial. An abutment 611 extends outwardly from the sounding board 610 which engages a plurality of teeth 211 formed circumferentially about the lower portion of the air flow tube 200 at the forward portion thereof adjacent to the inlet end 201 and the one-way flapper valve 205. In this manner, when the rotatable adjusting dial 200 is turned, an audible sound will be mechanically generated to signal that a change in position has occurred.

The rotatable adjusting dial 600 is mounted on the inlet end 201 of the flow tube 200 and is rotatable about the inlet end and held in contact therewith by the abutment 611 and a pair of guides 650 which provides three point contact between the rotatable adjusting dial 600 and the inlet end 201 of the air flow tube. The adjusting dial 600 is formed with a circumferential groove 660 and circumferential flange 661 which engage complementary formed flanges and grooves, 160 and 161, respectively, on the upper and lower housing portions 120 and 150, respectively, to secure the dial 600 to the air flow tube 220 and housing of the PEP device 1000. A guide tab 665 is carried by the flange 661 to extend into the lower housing portion 150 to guide the rotational movement of the adjusting dial 600. A boss 127 is carried at the forward portion of the upper housing 120 to prevent the expiratory air driven oscillatory rocker assembly 500 from being moved out of position or the cam follower tip 341 from moving out from engagement with the cam surfaces 641, 642. A plurality of bosses 126 are also formed on the housing portions 120 and 150 to strengthen the housing portions and to secure the internal components in their desired position.

When the air flow tube 200 with the expiratory air driven oscillatory rocker assembly 500 mounted thereon has the adjusting dial 600 positioned on the inlet end 201 with the cam follower tip 341 positioned between the two cam surfaces 641, 642, the assembly 500 is positioned into the lower housing 150, and the upper housing 120 installed thereover. A plurality of snap fittings 128 are formed on the upper housing 120 to engage receiving portions 158 formed on the lower housing 150 to secure the unit together.

INDUSTRIAL APPLICABILITY

During use of the variable frequency positive expiratory pressure device 1000, a patient inhales through the patient input end 202, drawing inspiratory air through the one-way valve 205 carried at the inlet end 201 of the air flow tube 220. The patient's expiratory air is then discharged into the patient input end 202, but must pass through the opening 326 of the adjustable orifice platform 310 because of the closure of the one-way valve 205 preventing air from flowing outwardly through the input end 201.

As the patient or user applies a positive expiratory air pressure at the patient input end 202, the air pressure is applied through the opening 326 against the cone 425 of the rocker assembly 400 which forms a closure of the opening 326. The pressure of the patient expiratory air will raise the cone 425, causing the rocker assembly 400 to pivot about its pivot pins 460 against the force of the magnetic field between the magnet 350 carried on the pivotal magnet support 330 and the steel pin 450 carried on the rocker assembly. As the cone 425 moves upwardly, the tapered configuration of the tapered conical interior 325 of the coupling 322 increases the effective discharge area thereby decreasing the patient induced expiratory air pressure applied against the cone 425. When the magnetic force and the venturi effect of the air flow overcome the air pressure applied to the cone 425, the cone will again move downwardly into the tapered conical surface 325 momentarily closing off the expiratory air flow through the opening 326. When this occurs, the back pressure to the patient or user is again increased causing another back pressure pulse. Upon this pressure increase, the expiratory air pressure will rise to again raise the tapered cone 425 out from engagement with the tapered conical surface 325 increasing the effective discharge area and reducing the pressure to repeat the cycle. In this manner a periodic positive pressure wave form is created as illustrated in FIGS. 14 and 15.

Figure 14:
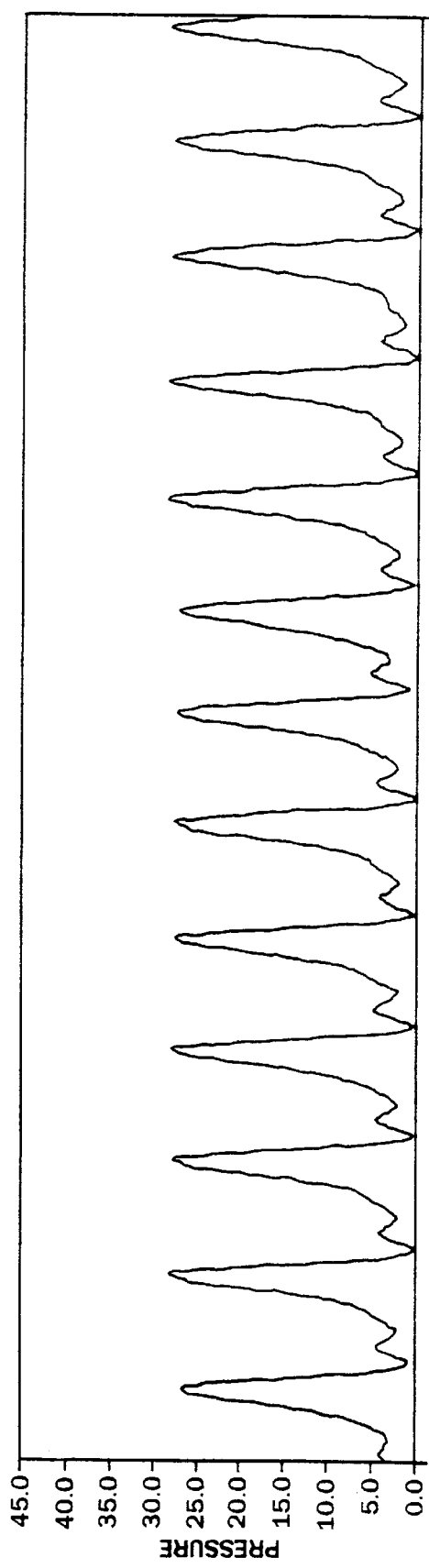
FIGS. 14 and 15 are, respectively, graphical representations of the operation of the invention under the same flow rate of expiratory air when the rotatable adjustment dial has been moved from a position wherein the oscillatory positive pressure and frequency are of a lower magnitude, in response to the positioning of the magnet as shown in solid lines in FIG. 13, to a position wherein the oscillatory positive pressure and frequency are of a higher magnitude in response to the positioning of the magnet as shown in the dashed lines in FIG. 13.
Figure 15:
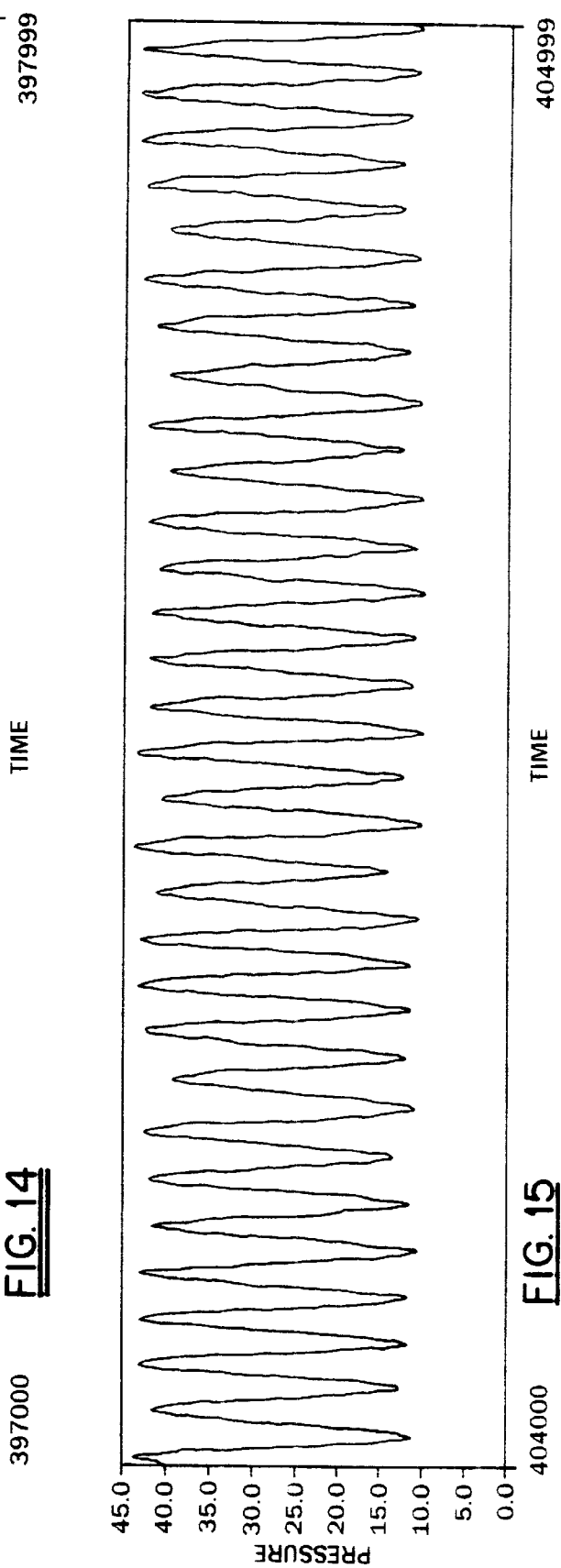

For a given air flow, when the magnetic field is decreased, by increasing the space between the magnet 350 and steel pin 450, the pulsating frequency and pressure will be low as illustrated in FIG. 14. As the adjusting dial 600 is turned to reduce the spacing between the magnet 350 and steel rod 450, the magnetic field will be increased, thereby creating a higher frequency and pressure pulsation. Rotation of the adjustable dial 600 between the limits of the cam surfaces 641, 642 allows the physician or clinician to set a desired frequency and pressure for an individual patient or user, and the desired frequency and pressure can be replicated by referring to the indicia 625 on the adjusting dial.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

What is claimed is:

1. A positive expiratory pressure therapy device for inducing an oscillatory expiratory air pressure from a patient, comprising an airflow tube having an inlet opening through which a patient to be treated inhales inspiratory air, and a patient input opening through which a patient inhales to draw inspiratory air into said air flow tube and through which a patient exhales to discharge expiratory from said air flow tube;

a one-way valve carried at said air flow tube inlet opening to allow inspiratory air to be drawn therethrough, but to block the passage of expiratory air therethrough;

said air flow tube further including a non-linear discharge orifice which is closed during the passage of inspiratory air through said inlet opening, and opened in response to the discharge of expiratory air; and control means for controlling the opening and closing of said non-linear discharge orifice in response to the pressure of the expiratory air discharged into said patient input opening.

2. The positive expiratory pressure therapy device of claim 1 wherein said control means includes an orifice closure normally closing said non-linear discharge orifice but operable to open said non-linear discharge orifice in response to the expiratory air pressure discharged into said patient input opening.

3. A positive expiratory pressure therapy device for inducing an oscillatory expiratory air pressure from a patient, comprising an airflow tube having an inlet opening through which a patient to be treated inhales inspiratory air, and a patient input opening through which a patient inhales to draw inspiratory air into said air flow tube and through which a patient exhales to discharge expiratory from said air flow tube;

a one-way valve carried at said air flow tube inlet opening to allow inspiratory air to be drawn therethrough, but to block the passage of expiratory air therethrough;

said air flow tube further including a non-linear discharge orifice which is closed during the passage of inspiratory air through said inlet opening, and opened in response to the discharge of expiratory air;

control means for controlling the opening and closing of said non-linear discharge orifice in response to the pressure of the expiratory air discharged into said patient input opening;

said control means including an orifice closure normally closing said non-linear discharge orifice but operable to open said non-linear discharge orifice in response to the expiratory air pressure discharged into said patient input opening; and said non-linear discharge orifice closure comprising a cone pivotally movable into and out from said non-linear discharge orifice in response to the pressure of the expiratory air discharged into said patient input opening.

4. The positive expiratory pressure therapy device of claim 3 wherein said control means includes a magnetic force field biasing said pivotally movable cone into a position for closing said non-linear discharge orifice.

5. The positive expiratory pressure therapy device of claim 4 further including means for adjusting the magnitude of the magnetic force field biasing said pivotally movable cone into a position for closing said non-linear discharge orifice.

6. A method of inducing an oscillatory expiratory air pulse in a patient using a positive expiratory air pressure therapy device, comprising:

passing a flow of patient-induced expiratory air into an air flow tube having a non-linear discharge orifice through which expiratory air is discharged;

interrupting the discharge of expiratory air through said non-linear discharge orifice by closing said orifice until the expiratory air pressure reaches a predetermined level;

opening said discharge orifice allowing the discharge of expiratory air therethrough until the pressure of the expiratory air discharged therethrough falls below said predetermined level; and applying a biasing force for closing said discharge orifice to control said predetermined level of expiratory air pressure.

7. A method of inducing an oscillatory expiratory air pulse in a patient using a positive expiratory air pressure therapy device, comprising:

passing a flow of patient-induced expiratory air into an air flow tube having a non-linear discharge orifice through which expiratory air is discharged;

interrupting the discharge of expiratory air through said non-linear discharge orifice by closing said orifice until the expiratory air pressure reaches a predetermined level;

opening said discharge orifice allowing the discharge of expiratory air therethrough until the pressure of the expiratory air discharged therethrough falls below said predetermined level; and applying a biasing force for closing said discharge orifice to control said predetermined level of expiratory air pressure by inducing a magnetic force field to control said predetermined level of expiratory air pressure.

8. The method of inducing an oscillatory expiratory air pulse in a patient using a positive expiratory air pressure therapy device of claim 7 wherein said step of applying a biasing force for closing said discharge orifice to control said predetermined level of expiratory air pressure includes applying a venturi induced force for closing said discharge orifice.

9. A positive expiratory pressure therapy device for inducing an oscillatory expiratory air pressure from a patient, comprising an airflow tube having an inlet opening through which a patient to be treated inhales inspiratory air, and a patient input opening through which a patient inhales to draw inspiratory air into said air flow tube and through which a patient exhales to discharge expiratory from said air flow tube;

a one-way valve carried at said air flow tube inlet opening to allow inspiratory air to be drawn therethrough, but to block the passage of expiratory air therethrough;

said air flow tube further including a non-linear discharge orifice which is closed during the passage of inspiratory air through said inlet opening, and opened in response to the discharge of expiratory air;

control means for controlling the opening and closing of said non-linear discharge orifice in response to the pressure of the expiratory air discharged into said patient input opening;

said control means including an orifice closure normally closing said non-linear discharge orifice but operable to open said non-linear discharge orifice in response to the expiratory air pressure discharged into said patient input opening; and said non-linear discharge orifice closure comprising a cone movable into and out from said non-linear discharge orifice in response to the pressure of the expiratory air discharged into said patient input opening.

* * * * *